(12) United States Patent
Ouchi (10) Patent No.: US 6,423,054 B1
(45) Date of Patent: Jul. 23, 2002

(54) OPERATION WIRE CONNECTING PART IN ENDOSCOPIC TREATING INSTRUMENT

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 136 days.

(21) Appl. No.: 09/618,051

(22) Filed: Jul. 17, 2000

(30) Foreign Application Priority Data

Aug. 4, 1999 (JP) ............................................. 11-221131

(51) Int. Cl.⁷ ............................................... A61B 17/00
(52) U.S. Cl. .............................. 606/1; 606/46; 600/117; 604/22
(58) Field of Search ........................ 606/1, 46; 600/104, 600/117, 146; 604/22

(56) References Cited

U.S. PATENT DOCUMENTS 5,766,184 A * 6/1998 Matsuno et al. ............ 606/142
5,849,022 A * 12/1998 Sakashita et al. ........... 606/174
6,162,207 A * 12/2000 Ouchi ........................... 606/1

FOREIGN PATENT DOCUMENTS

| JP | 58160010 | 10/1983 |
| JP | 60-31684 | 9/1985 |
| JP | 61-4326 | 2/1986 |
| JP | 63-65852 | 3/1988 |

* cited by examiner

*Primary Examiner*—Denise L. Esquivel
*Assistant Examiner*—Marc Norman
(74) *Attorney, Agent, or Firm*—Greenblum & Bernstein, P.L.C.

(57) ABSTRACT

In an operation wire connecting part of an endoscopic treating instrument, an engaging groove is formed for engagement with a small diameter portion of a connecting rod at a base end of an operation wire. Widths of small width portions of the engaging groove are made different according to locations where the small width portions are formed in the engagement groove to make it possible to selectively engage the engagement groove with plural types of the connecting rods having respective small diameter portions of different diameters.

10 Claims, 7 Drawing Sheets

OPERATION WIRE CONNECTING PART IN ENDOSCOPIC TREATING INSTRUMENT

BACKGROUND OF THE INVENTION

The present invention relates to an operation wire connecting part in an endoscopic treating instrument.

Generally, the endoscopic treating instrument is so constructed that an operation wire is disposed in a sheath so as to move back and forth in an axial direction, and an operating section for manipulating the operation wire to move it back and forth in an axial direction is connected to a base end of the sheath. In not a few endoscopic treating instrument, the sheath and the operation wire which are, so to speak, consumable items are detachably constructed with respect to the operating section.

The operation wire connecting part in most of the endoscopic treating interments is so constructed that a connecting rod attached to a base end portion of the operation wire which has been drawn out from the base end of the sheath is passed through an engaging groove formed in an operating member, and the engaging groove is moved in a direction perpendicular to an axis of the connecting rod allowing a small width portion of the engaging groove to be engaged with a small diameter portion formed in the connecting rod, whereby the connecting rod is adapted to move integrally with the operating member.

Generally, there have been prepared a plurality of endoscopic treating instruments, for the same type of treatment, having respective different diameters of the sheathes and the operation wires so as to match with a selected endoscope to be used. That is, a suitable one of endoscopic treating instruments is selected depending on the selected one of endoscopes having respective different diameters of treating instrument insertion channels, so that the sheath and operation wire in the selected endoscopic treating instrument match in diameter with the treating instrument insertion channel of the selected endoscope.

As the sheathes and the operation wires are different in diameter, outer diameters of the small diameter portions of the connecting rods respectively fixed to the base ends of the operation wires are different, and the widths of the engaging grooves in the respective operating sections to be engaged with the small diameter portions are also different. For this reason, it is necessary to separately prepare various types of the operating sections having respective different widths of the engaging grooves to match with the diameters of the sheathes and the operation wires. This requires complicated and cumbersome handling.

SUMMARY OF THE INVENTION

In view of the above, it is an object of the invention to provide an operation wire connecting part in an endoscopic treating instrument which can be commonly used for and connectable to sheathes and the operation wires having different diameters, thereby providing flexibility.

According to the invention, because width of a small width portion of the engaging groove is made different according to positions, so that plural types of the connecting rods having the small diameter portions which are different in diameter can be selectively engaged with the engaging groove. Therefore, the treating instruments in which the diameters of the sheathes and the operation wires are different can be connected to the same operating section for use, and the general versatility or flexibility of the operating section can be greatly enhanced.

An operation wire connecting part in an endoscopic treating instrument according to a preferred embodiment the invention is so constructed that a base end of an operation wire passed through a sheath axially movably is drawn out from a base end of the sheath, a connecting rod on the base end of the operation wire is passed through an engaging groove provided in an operating member for manipulating the operation wire to move it back and forth in an axial direction, and the engaging groove is moved in a direction perpendicular to an axis of the connecting rod allowing a small width portion of the engaging groove to be engaged with a small diameter portion formed in the connecting rod, whereby the connecting rod is adapted to move integrally with the operating member. In the connecting part of the preferred embodiment, the small width portion of the engaging groove is made different in width according to positions, thereby enabling plural types of the connecting rods having different diameters at their small diameter portions to be engaged with the engaging groove.

The width of the small width portion of the engaging groove may vary as a plurality of steps in a stepwise manner, or may gradually vary.

Preferably, the engaging groove may be biased in a direction where the connecting rod is positively engaged with the small width portion so as to prevent the disengagement of the connecting rod from the engaging groove.

The present disclosure relates to the subject matter contained in Japanese patent application No. Hei. 11-221131 (filed on Aug. 4, 1999), which is expressly incorporated herein by reference in its entirety.

DESCRIPTION OF THE PREFERRED EMBODIMENT

Referring to the drawings, Preferred embodiments of the invention will be described.

Figure 3:
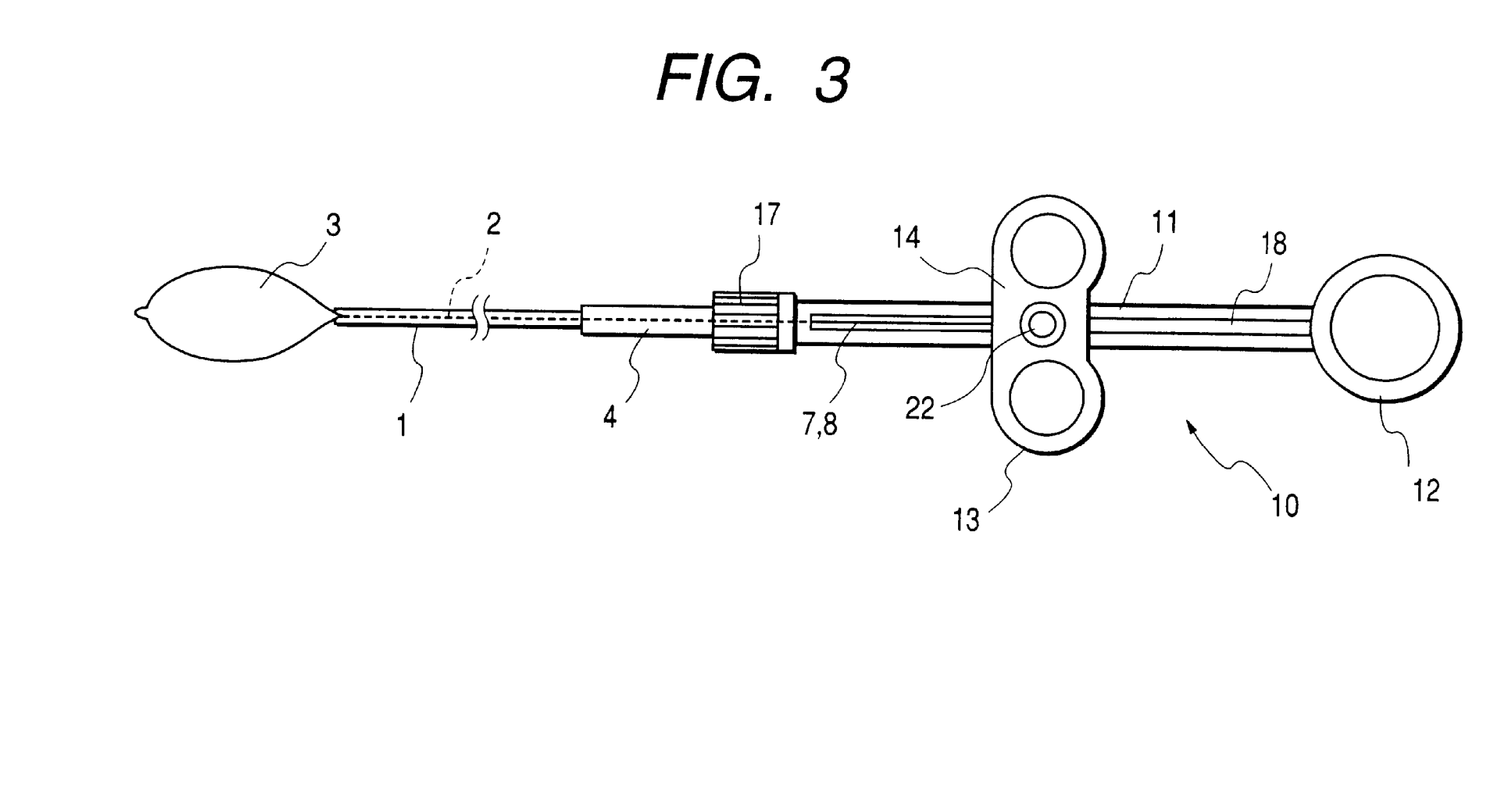
FIG. 3 is a plan view showing an entire structure of the endoscopic high frequency treating instrument according to the first embodiment of the invention.

FIG. 3 shows a high frequency snare which is one of endoscopic high frequency treating instruments. However, the invention can be applied to various other types of endoscopic treating instruments.

A flexible sheath 1 adapted to be inserted into and removed from a treating instrument insertion channel in an endoscope, which is not shown, is formed of an electrically insulating tube such as a tetrafluoroethylene resin tube.

Disposed inside the flexible sheath 1 is an electrically conductive operation wire 2 passing through the entire length of the flexible sheath 1 movably back and forth in an axial direction. By moving the operation wire 2 back and forth, an electrically conductive snare loop 3 connected to a forward end of the operation wire 2 is projected from and retracted into a forward end of the flexible sheath 1 to expand and contract by its self elasticity. Numeral 4 designates a bending prevention tube for preventing a base end portion of the flexible sheath 1 from being extremely bent and broken.

An operating section 10 for manipulating the operation wire 2 to move it back and forth is connected to the base end of the flexible sheath 1. As described below, the flexible sheath 1 and the operation wire 2 can be freely connected to and detached from the operating section 10.

An operating section main body 11 in a form of a rod is provided at its rearward end with a first finger hook 12 to be engaged with an operator's thumb. A slider (an operating member) 14 is provided with second finger hooks 13 to be engaged with his index finger and middle finger, and is slidably mounted along the operating section main body 11.

Figure 2:
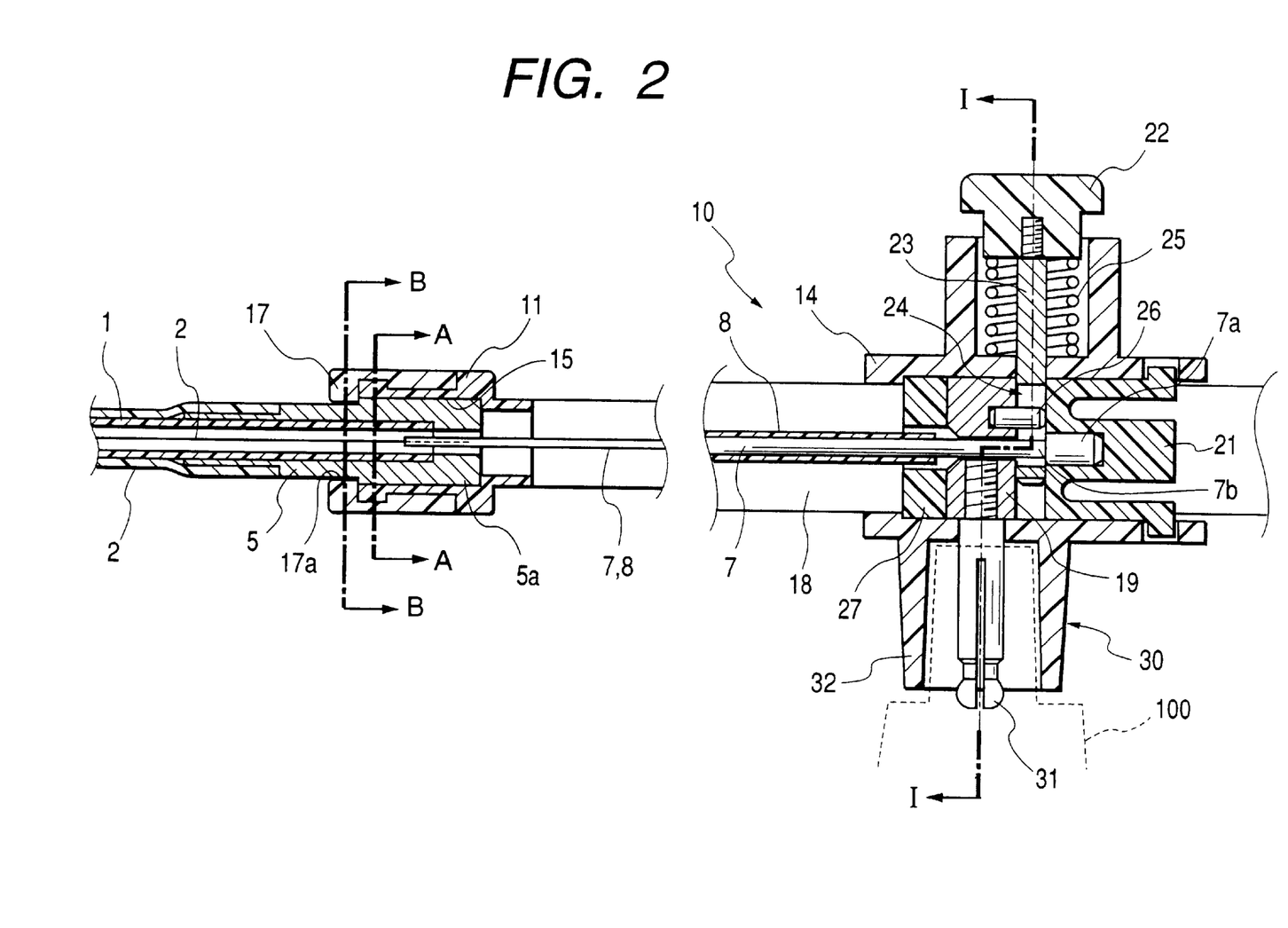
FIG. 2 is a partially enlarged sectional view of an operating section in an endoscopic high frequency treating instrument according to the first embodiment of the invention.

FIG. 2 shows the operating section 10 partially enlarged. Numeral 5 designates a base end joint attached to the base end of the flexible sheath 1 and inserted into a square hole 15 which is formed in a forward end of the operating section main body 11.

A connecting and fixing pipe 17 for connecting and fixing the base end joint 5 to the operating section main body 11 is fitted to the forward end portion of the operating section main body 11 in an embracing manner so as not to move in an axial direction but to rotate about an axis by 45 degree, for example.

Figure 4:
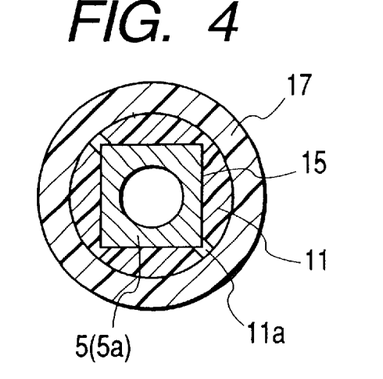
FIG. 4 is a sectional view of the first embodiment according to the invention taken along a line A—A in FIG. 2.

FIG. 4 is a sectional view taken along a line A—A in FIG. 2, wherein an interior of the base end joint 5 is omitted to be shown. The forward end portion of the operating section main body 11 is provided with slits 11a in a direction parallel to an axis thereof at an interval of 90 degree for example, and so, the connecting and fixing pipe 17 can be fitted to the operating section main body 11 by elastically deforming the slitted portion inwardly in a state where the base end joint 5 is removed.

Figure 5:
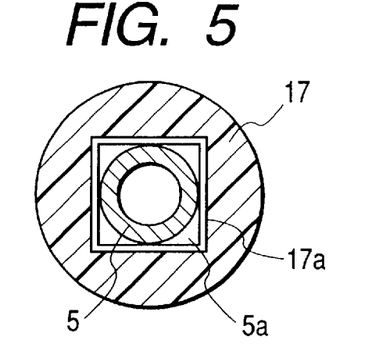
FIG. 5 is a sectional view of the first embodiment according to the invention taken along a line B—B in FIG. 2 when a connecting and fixing pipe is in an unfixed state.

As shown in FIG. 5 which is a sectional view taken along a line B—B in FIG. 2, a front end wall of the connecting and fixing pipe 17, is formed with a square hole 17a through which a square shaft portion 5a of the base end joint 5 passes. Through the square hole 17a, the square shaft portion 5a of the base end joint 5 can be inserted into a square hole 15 which is formed inside the operating section main body 11.

Figure 6:
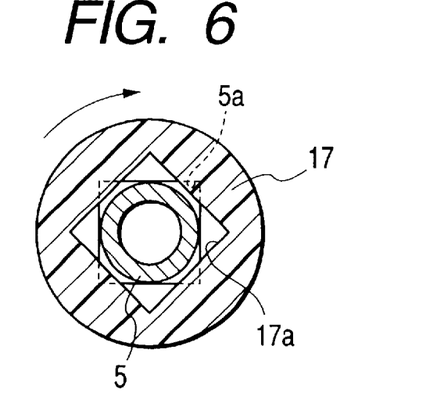
FIG. 6 is a sectional view of the first embodiment according to the invention taken along a line B—B in FIG. 2 when the connecting and fixing pipe is in a fixed state.

Consequently, the base end mouthpiece 5 can be engaged with and disengaged from the operating section main body 11. By rotating the connecting and fixing pipe 17 by 45 degree as shown in FIG. 6 which is a sectional view taken along the line B—B, the square hole 17a of the connecting and fixing pipe 17 is put in a position where the square shaft portion 5a of the base end joint 5 can not pass through the square hole 17a, thereby making the base end joint 5 locked with the operating section main body 11.

Figure 1:
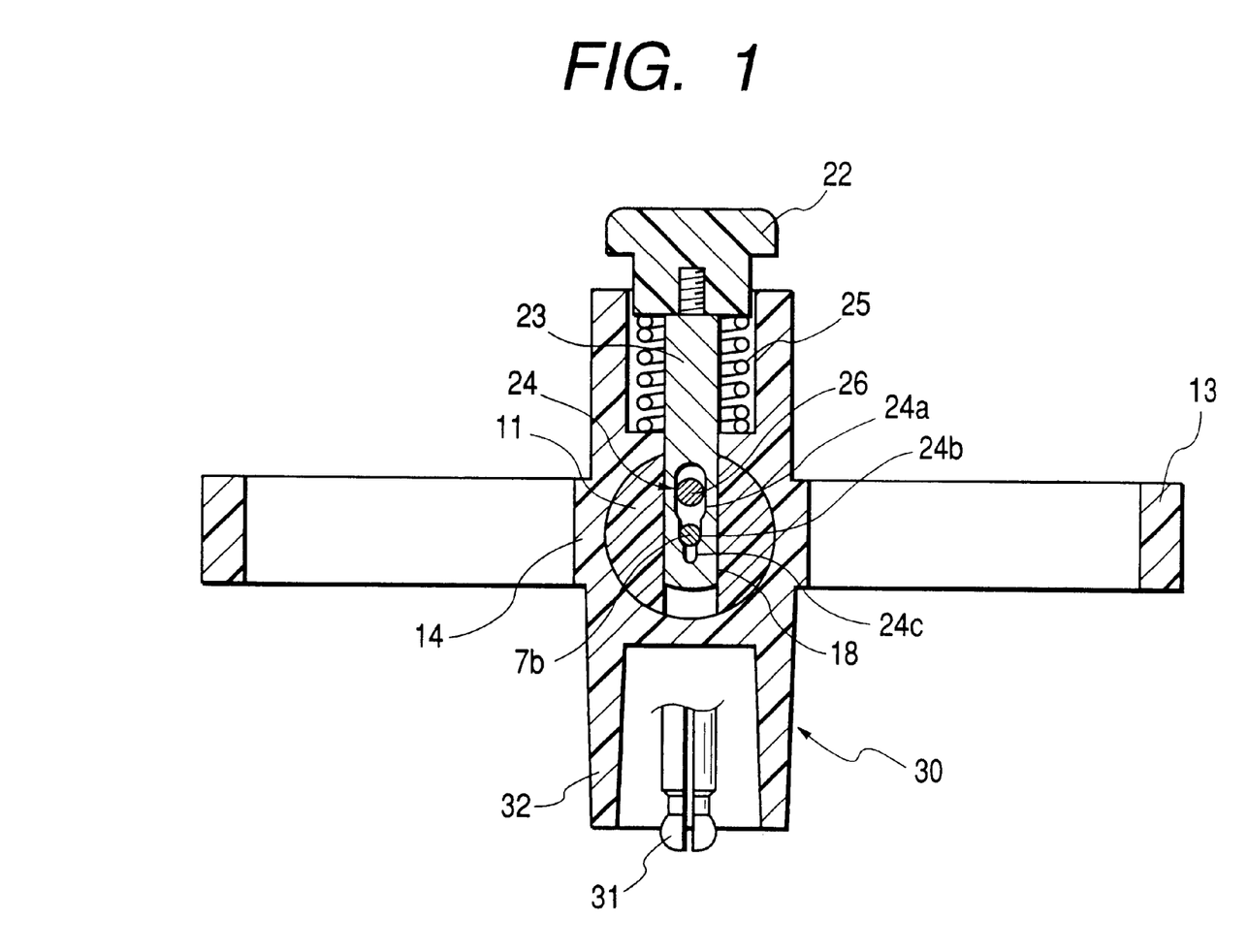
FIG. 1 is a sectional view of a first embodiment according to the invention taken along a line I—I in FIG. 2.

In a right half part of FIG. 2, there is shown an engaging part of the slider 14 with respect to the operating section main body 11. FIG. 1 is a sectional view taken along a line I—I in FIG. 2.

The operation wire 2 passing through the flexible sheath 1 is drawn out from the base end of the flexible sheath 1. A connecting rod 7 made of an electrically conductive metal bar is fixed to a base end of the operation wire 2. The connecting rod 7 extends on and along a central position (that is, a position of an axis of the operating section main body 11) of a slot 18 which is longitudinally formed in the operating section main body 11.

Numeral 21 designates an electrically insulating block which is held in the slot 18 in such a manner that it is embraced by the slider 14. A retaining portion 7a having a large diameter (a large diameter portion) is formed at a base end of the connecting rod 7, and is inserted into a blind hole formed at a central position of the insulating block 21.

Numeral 22 designates a lock release button for locking and releasing the connecting rod 7 with respect to the slider 14. A slide plate 23 is connected to align with a position of an axis of the lock release button 22. The slide plate 23 is provided with an engaging groove 24 for engagement with the connecting rod 7.

As shown in FIG. 1, the engaging groove 24 includes a large width portion 24a through which the retaining portion 7a of the connecting rod 7 can pass, and a first small width portion 24b that continues from the large width portion 24a and that has such a width that the retaining portion 7a cannot pass but a small diameter portion 7b adjacent to the retaining portion 7a can pass therethrough. The engaging groove 24 further includes a second small width portion 24c that continues from the first small width portion 24b and that is smaller in width than the first small width portion 24b.

The lock release button 22 is biased outwardly by means of a helical compression spring 25. When the lock release button 22 is pushed inwardly against a force of the helical compression spring 25, the slide plate 23 is set in such a position that the retaining portion 7a passes through the large width portion 24a of the engaging groove 24. Consequently, the base end of the connecting rod 7 can be engaged with and disengaged from the slider 14.

When the operator s finger is detached from the lock release button 22, the slide plate 23 moves in a direction perpendicular to the axis of the connecting rod 7 to set the connecting rod 7 at the small width portion 24b of the engaging groove 24 through which the retaining portion 7a is unable to pass. Thus, the base end of the connecting rod 7 comes into a fixed condition with respect to the slider 14.

Therefore, by manipulating the slider 14 to move it back and forth in this state, the operation wire 2 simultaneously moves so that the snare loop 3 at the forward end of the flexible sheath 1 can be operated remotely. Numeral 26 designates an electrically conductive pin which is projectingly formed on an electrically conductive terminal receiving member 19 so as to be engaged with the engaging groove 24 for preventing removal of the slide plate 23, guiding the slide plate 23 and electrically connecting the terminal receiving member to the connecting rod 7.

The slider 14 is provided with a terminal 30 to be connected to a high frequency electric source at a face opposite to the lock release button 22. Numeral 31 designates an contact pin and numeral 32 designates an insulating pipe which is integrally formed with the slider 14.

The contact pin 31 made of an electrically conductive metal is screwed into the terminal receiving member 19 which is disposed in the slot 18. By connecting a connecting plug 100 of a high frequency electric source cord, which is shown by a dotted line, to the high frequency electric source connecting terminal 30, a high frequency electric current can be transmitted from the contact pin 31 through the terminal receiving member 19, the slide plate 23, the connecting rod 7, and the operation wire 2, to the snare loop 3.

A back end face of the terminal receiving member 19 through which the high frequency electric current flows inside the slider 14 is covered with the above described insulating block 21, while a front end face of the terminal receiving member 19 is covered with an electrically insulating board 27 which is clamped and fixed between the terminal receiving member 19 and a stepped portion of the slider 14.

The entire length of the connecting rod 7 is covered with an electrically insulative tube 8 such as a tetrafluoroethylene resin tube. The above described lock release button 22 attached to a top end of the slide plate 23 is formed of an electrically insulating plastic material.

Figure 7:
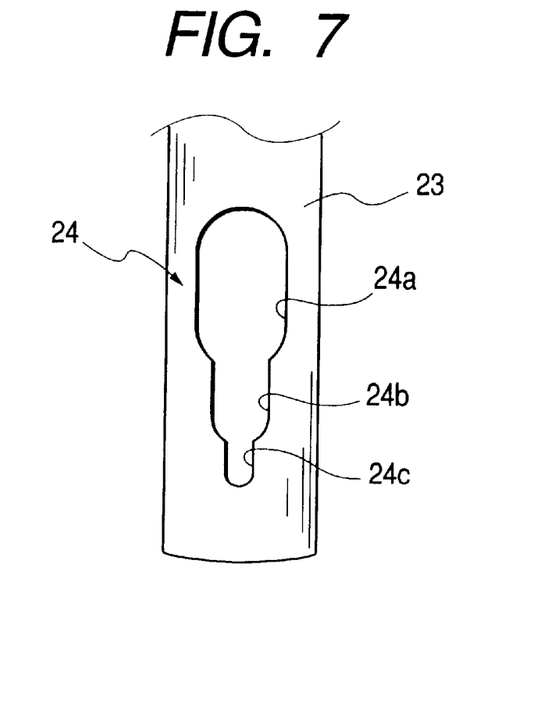
FIG. 7 is a front view of a slide plate according to the first embodiment of the invention.

FIG. 7 shows the slide plate 23 alone. The engaging groove 24 formed therein includes the first small width portion 24b in continuation with the large width portion 24a, and further, a second smaller width portion 24c which is in continuation with the first small width portion 24b and smaller than the first small width portion 24b. These large width portion 24a, the first small width portion 24b and the second small width portion 24c are formed in the slide plate 23 in a stepwise manner.

Figure 8:
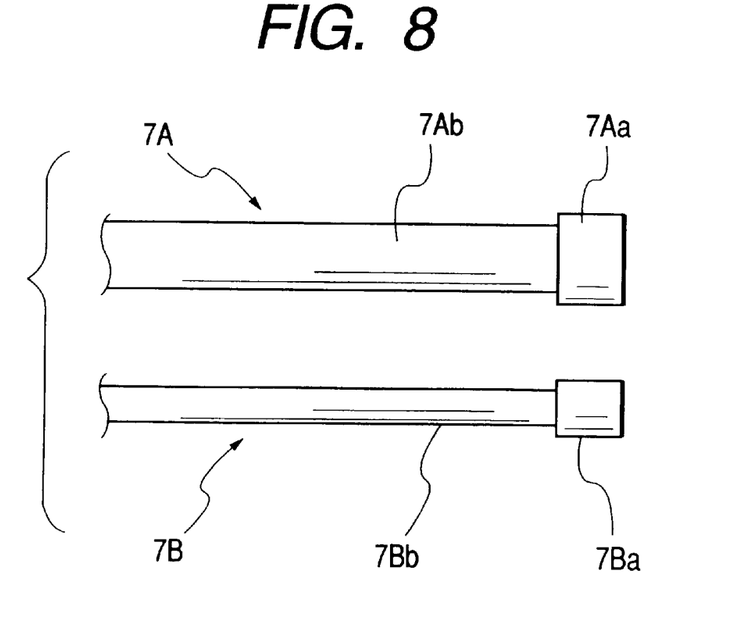
FIG. 8 is a side view showing two connecting rods having different diameters.

FIG. 8 shows a first connecting rod 7A and a second connecting rod 7B having respective different diameters. The dimensional relationship between the first connecting rod 7A and the engaging groove 24 is as follows: The large diameter portion 7Aa of the first connecting rod 7A can pass through the large width portion 24a, but cannot pass through the first small width portion 24b, and the small diameter portion 7Ab can pass through the first small width portion 24b but cannot pass through the second smaller width portion 24c.

The dimensional relationship between the second connecting rod 7B and the engaging groove 24 is as follows: The large diameter portion 7Ba of the second connecting rod 7B can pass through the first small width portion 24b, but cannot pass through the second smaller width portion 24c, and the small diameter portion 7Bb can pass through the second smaller width portion 24c.

Figure 9:
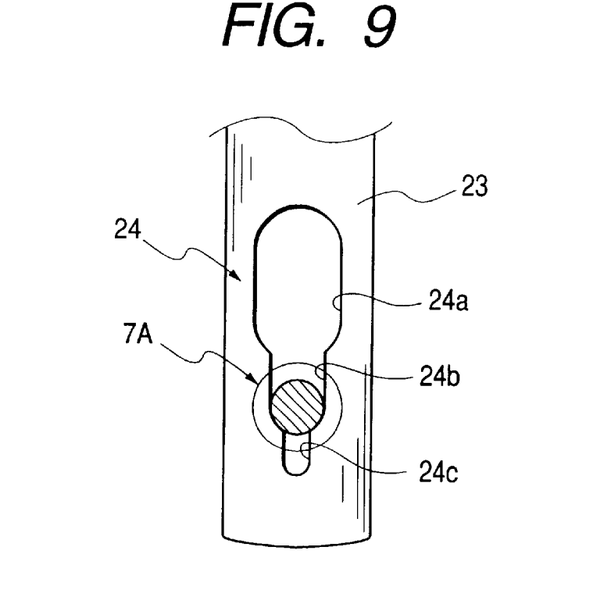
FIG. 9 is a sectional front view showing the slide plate of the operation wire connecting part in the endoscopic treating instrument in the first embodiment of the invention in a state where a first connecting rod is engaged with the slide plate.
Figure 10:
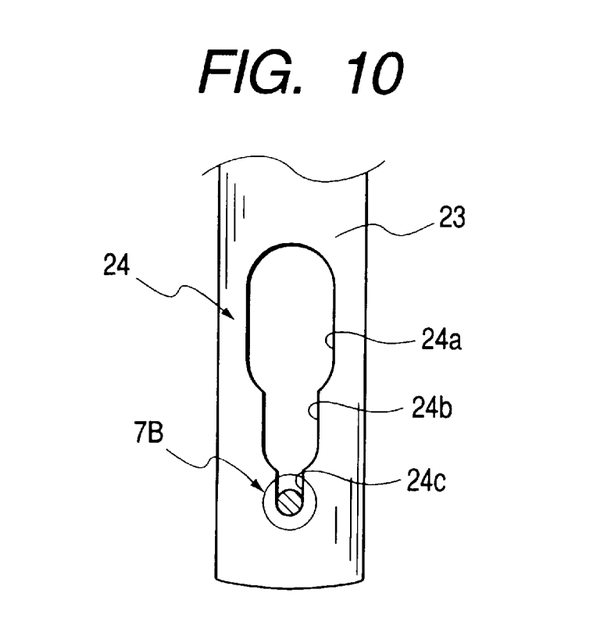
FIG. 10 is a sectional front view showing the slide plate of the operation wire connecting part in the endoscopic treating instrument in the first embodiment of the invention in a state where a second connecting rod is engaged with the slide plate.

Accordingly, the treating instrument in which the first connecting rod 7A is fitted to the operation wire 2 can be used by engaging the connecting rod 7A with the first small width portion 24b of the engaging groove 24 as shown in FIG. 9, while the treating instrument in which the second connecting rod 7B is fitted to the operation wire 2 can be used in combination with the same operating section 10 by engaging the connecting rod 7B with the second smaller width portion 24c of the engaging groove 24 as shown in FIG. 10.

Therefore, even though the treating instruments have the connecting rods 7 different in diameter because of, for instance, different diameters of the flexible sheaths 1 and the operation wires 2, these treating instruments can be selectively used in combination with the common operating section 10 by connecting the connecting rod to the operating section 10. Thus, general versatility or flexibility of the operation section 10 can be enhanced.

Figure 11:
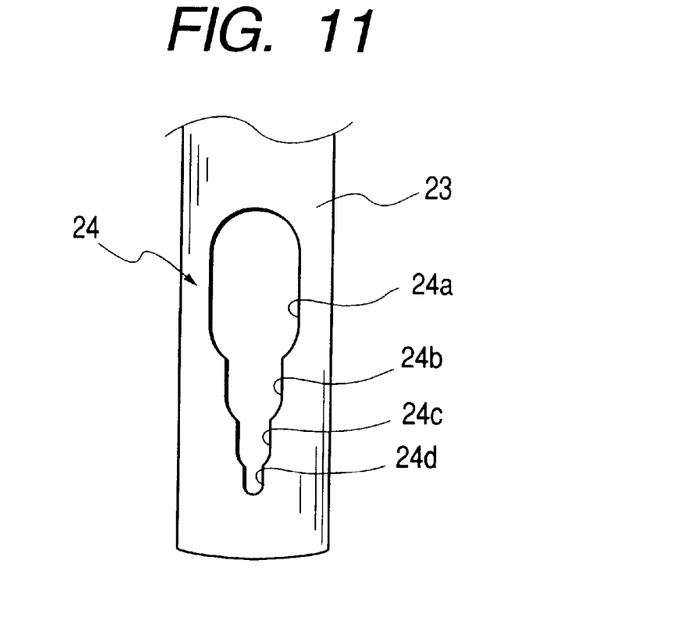
FIG. 11 is a front view of the slide plate according to a second embodiment of the invention.
Figure 12:
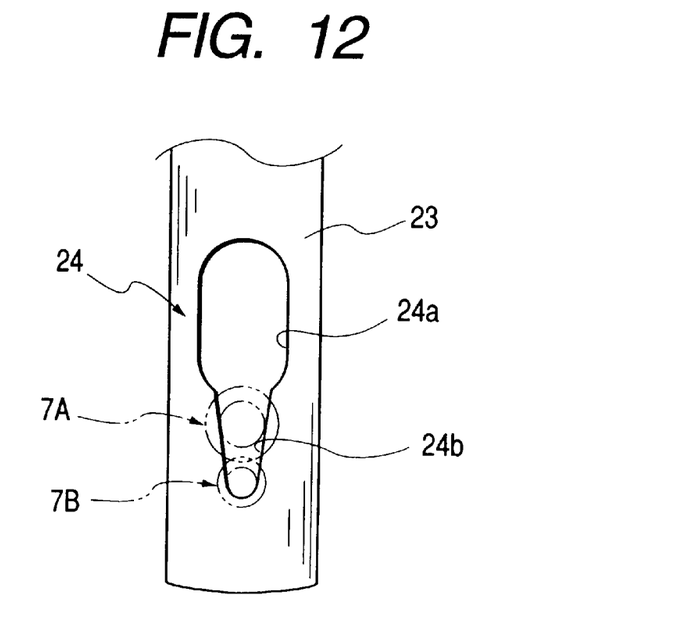
FIG. 12 is a front view of the slide plate according to a third embodiment of the invention.

It is to be noted that the invention is not limited to the above described embodiment. For example, the engaging groove 24 may have three or more small width portions (in FIG. 11, another embodiment in which three small width portions 24b, 24c and 24d are provided is shown) formed in a stepwise manner. Moreover, the small width portion 24b may be formed in a tapered shape gradually reducing in width in a direction away from the large width portion 24a, as shown in FIG. 12, so that the connecting rods 7A and 7B having different diameters can be engaged with the engaging groove 24 at respective positions.

What is claimed is:

1. An operation wire connecting part in an endoscopic treating instrument so constructed that a base end of an operation wire passed through a sheath axially movably is drawn out from a base end of said sheath, a connecting rod connected to the base end of said operation wire is passed through an engaging groove provided in an operating member for manipulating said operation wire to move it back and forth in an axial direction, and said engaging groove is moved in a direction perpendicular to an axis of said connecting rod allowing a small width portion of said engaging groove to be engaged with a small diameter portion formed in said connecting rod, whereby said connecting rod is adapted to move integrally with said operating member, wherein the small width portion of said engaging groove is made different in width according to positions, thereby making plural types of said connecting rods having respective different diameters at their small diameter portions engageable with said engaging groove.

2. An operation wire connecting part in an endoscopic treating instrument as claimed in claim 1, wherein the width of said small width portion of said engaging groove varies as a plurality of steps.

3. An operation wire connecting part in an endoscopic treating instrument as claimed in claim 1, wherein the width of the small width portion of said engaging groove gradually varies.

4. An operation wire connecting part in an endoscopic treating instrument as claimed in claim 1, wherein said engaging groove is biased in a direction where said connecting rod is engaged with said engaging groove so that the said connecting rod is not disengaged from said engaging groove.

5. An operation wire connecting part, provided in an endoscopic treating instrument, for connecting a desired one of operation wires having respective, differently-dimensioned connecting rods to a slider, said connecting part comprising:

a slide plate movably supported by the slider to extend across the connecting rod of the desired one of the operating wires;

an engaging groove formed through the slide plate to permit the connecting rod of the desired one of the operating wires to be passed through the slide plate, wherein the engaging groove includes:

a large width portion for permitting the connecting rods of all of the operation wires to be passed through the slider;

a first small width portion, continuing from the large width portion, for engagement with a first one of the connecting rods; and a second small width portion, continuing from the first small width portion, for engagement with a second one of the connecting rods that is smaller in diameter than the first one of the connecting rods.

6. An operation wire connecting part as claimed in claim 5, wherein the engaging groove further includes a third small width portion, continuing from the second small width portion, for engagement with third one of the connecting rods that is smaller in diameter than the second one of the connecting rods.

7. An operation wire connecting part as claimed in claim 5, wherein the first and second small width portions are provided in the engaging groove in a stepwise manner.

8. An operation wire connecting part as claimed in claim 5, wherein the engaging groove has a tapered portion gradually decreasing in width, and the taper portion defines the first and second small width portions.

9. An operation wire connecting part as claimed in claim 5, further comprising:

a spring, on the slider, for biasing the slide plate to move the large width portion away from the connecting rod of the desired one of the operation wires.

10. An operation wire connecting parts as claimed in claim 5, wherein the large width portion is larger in width than the first small width portion, and the first small width portion is larger in width than the second small width portion.

* * * * *